United States Patent
Hedberg et al.

(10) Patent No.: US 6,880,379 B2
(45) Date of Patent: Apr. 19, 2005

(54) METHOD AND DEVICE FOR DETECTING DAMAGE IN MATERIALS OR OBJECTS

(75) Inventors: Claes Hedberg, Karlskrona (SE); Alexander Sutin, Hoboken, NJ (US); Paul A. Johnson, Santa Fe, NM (US)

(73) Assignee: Impressonic AB (SE)

( * ) Notice: Subject to any disclaimer, the term of this patent is extended or adjusted under 35 U.S.C. 154(b) by 6 days.

(21) Appl. No.: 10/473,726

(22) PCT Filed: Feb. 14, 2002

(86) PCT No.: PCT/SE02/00259
§ 371 (c)(1),
(2), (4) Date: Oct. 1, 2003

(87) PCT Pub. No.: WO02/079775
PCT Pub. Date: Oct. 10, 2002

(65) Prior Publication Data
US 2004/0134280 A1 Jul. 15, 2004

(30) Foreign Application Priority Data
Apr. 2, 2001 (SE) ............................................. 0100495

(51) Int. Cl.[7] .......................... G01M 7/02; G01M 7/06; G01N 29/04; G01N 25/72; G01N 29/12
(52) U.S. Cl. .......................... 73/12.01; 73/579; 702/38; 702/39; 702/40
(58) Field of Search ................................ 73/12.01, 579, 73/602, 658, 659; 702/35, 38, 39, 40

(56) References Cited
U.S. PATENT DOCUMENTS

| | | | |
|---|---|---|---|
| 3,958,450 A | 5/1976 | Kleesattel | 73/67.2 |
| 4,689,993 A | 9/1987 | Slettemoen | 73/579 |
| 4,944,185 A | 7/1990 | Clark, Jr. et al. | 73/579 |
| 5,086,775 A * | 2/1992 | Parker et al. | 600/453 |
| 5,099,848 A * | 3/1992 | Parker et al. | 600/443 |
| 5,144,838 A | 9/1992 | Tsuboi | 73/579 |
| 5,214,960 A | 6/1993 | Tsuboi | 73/579 |
| 5,216,921 A | 6/1993 | Tsuboi | 73/579 |
| 5,284,058 A | 2/1994 | Jones | 73/579 |
| 5,327,358 A * | 7/1994 | Stubbs | 702/36 |
| 5,355,731 A | 10/1994 | Dixon et al. | 73/579 |
| 5,425,272 A | 6/1995 | Rhodes et al. | 73/579 |

(Continued)

FOREIGN PATENT DOCUMENTS

| WO | WO 99/39194 A1 | 8/1999 |
|---|---|---|
| WO | WO 00/34750 A1 | 6/2000 |

OTHER PUBLICATIONS

James A. TenCate, et al. "Universal Slow Dynamics in Granular Solids". In: Physical Review Letters. vol. 85, No. 5. Jul. 31, 2000. pp. 1020–1023.

(Continued)

Primary Examiner—Hezron Williams
Assistant Examiner—Rose M. Miller
(74) Attorney, Agent, or Firm—Ostrolenk, Faber, Gerb & Soffen, LLP

(57) ABSTRACT

In a method of detecting damage in materials or objects (4) the material or object is physically influenced to produce a physical change of the material or object inducing transient slow dynamics in case of damages in the material or object. Slow dynamics induced material elastic modulus changes are detected as indication of damages of the material or object. In a device for non-destructive detection of damage in materials or objects (4), an impact source (16) is provided to impact the material or object to physically influence the material or object to produce a physical change of the material or object inducing transient slow dynamics in case of damages in the material or object. A detector (2,8,10,12, 14,6) is provided to detect by said slow dynamics induced material elastic modulus changes as indications of damages of the material or object.

37 Claims, 11 Drawing Sheets

U.S. PATENT DOCUMENTS

| | | | |
|---|---|---|---|
| 5,520,052 A | 5/1996 | Pechersky | 73/579 |
| 5,528,924 A | 6/1996 | Wajid et al. | 73/24.06 |
| 5,719,860 A | 2/1998 | Maison et al. | 370/347 |
| 5,732,642 A | 3/1998 | DeSilva | 114/103 |
| 5,777,891 A | 7/1998 | Pagano et al. | 364/507 |
| 6,023,980 A | 2/2000 | Owen et al. | 73/797 |

OTHER PUBLICATIONS

A.S. Korotkov and A.M. Sutin, "Modulation of Ultrasound by Vibrations in Metal Construction with Cracks" Aconstics Letter, vol. 18, No. 4, 1994, pp. 59–62.

Robert A. Guyer and Paul A. Johnson "Nonlinear Mesoscopic Elasticity: Evidence for a New Class of Materials" Physics Today, Apr. 1999, pp. 30–36.

* cited by examiner

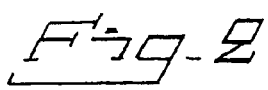
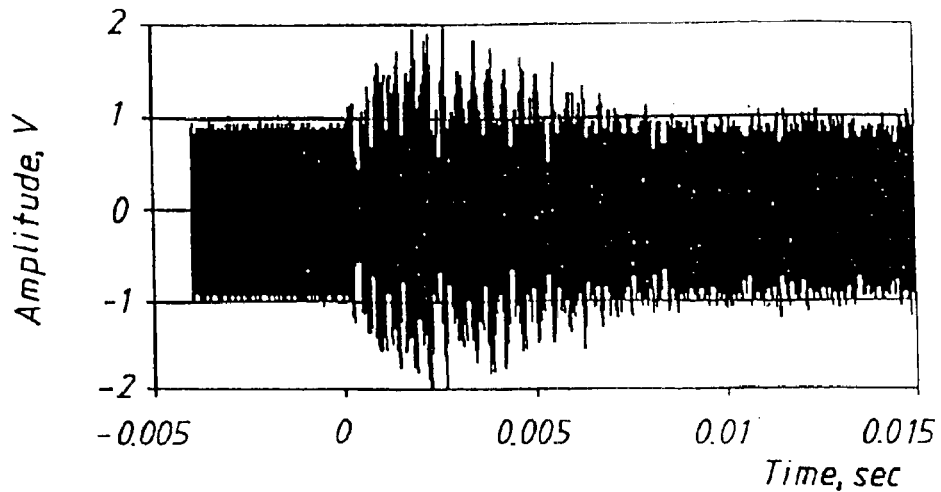
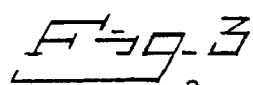
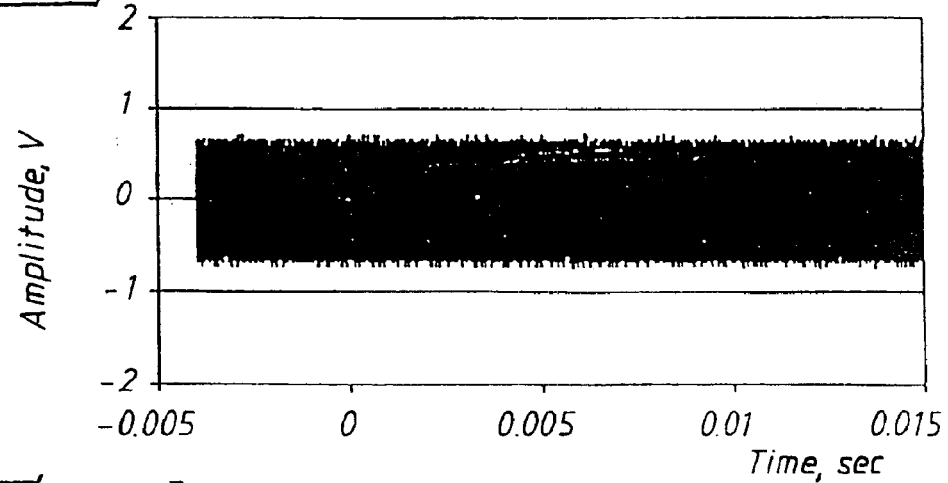
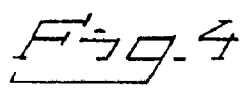
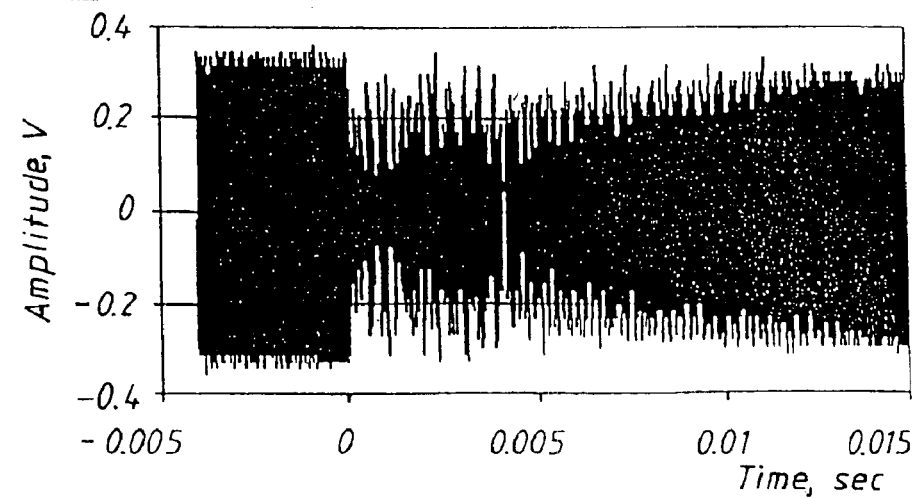

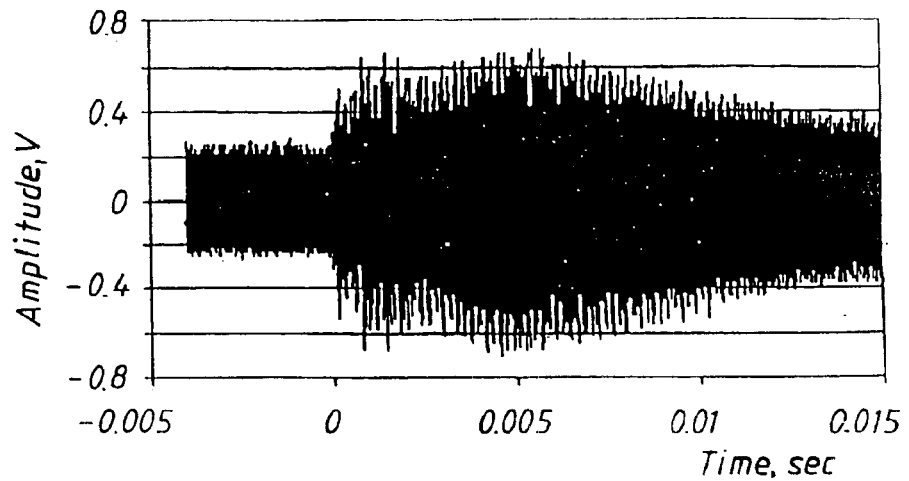
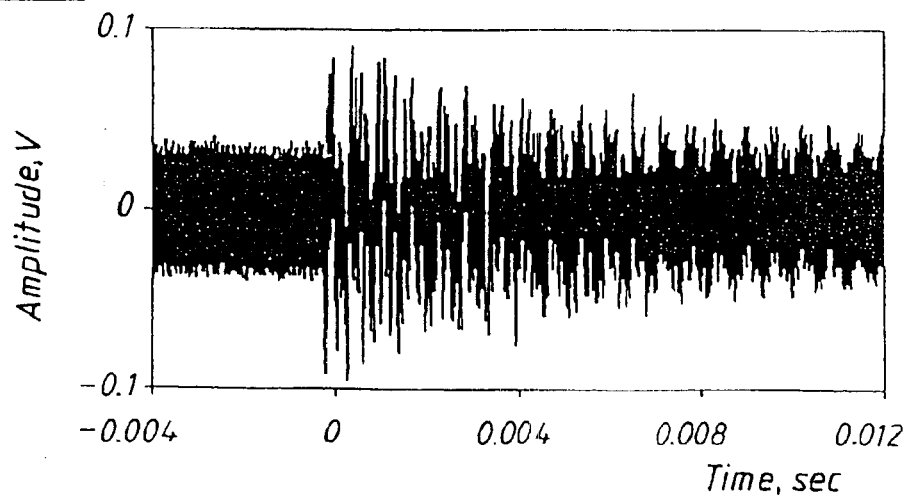
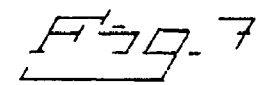
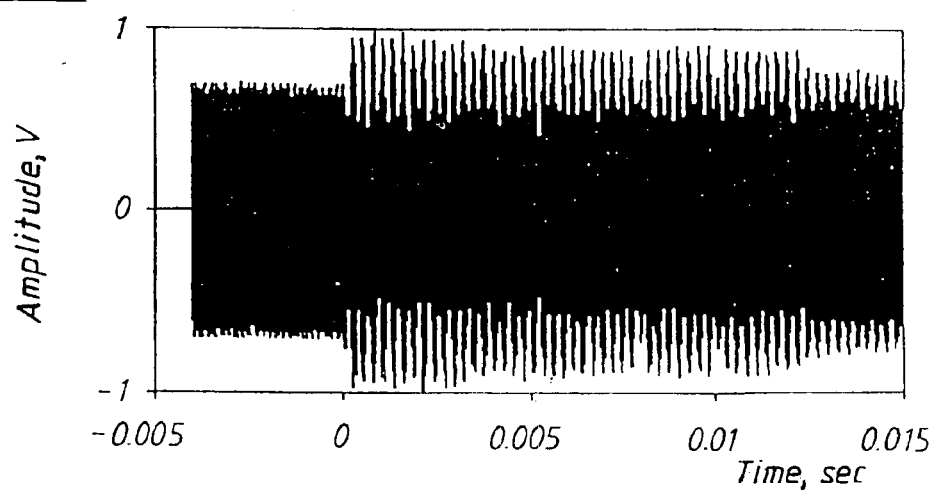

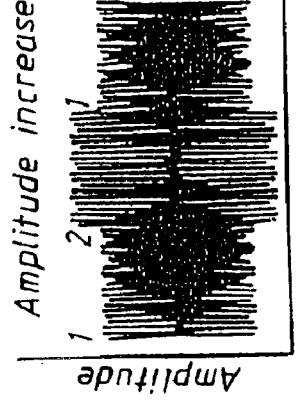
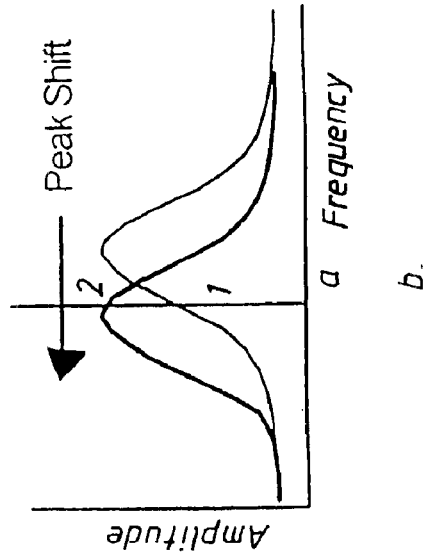
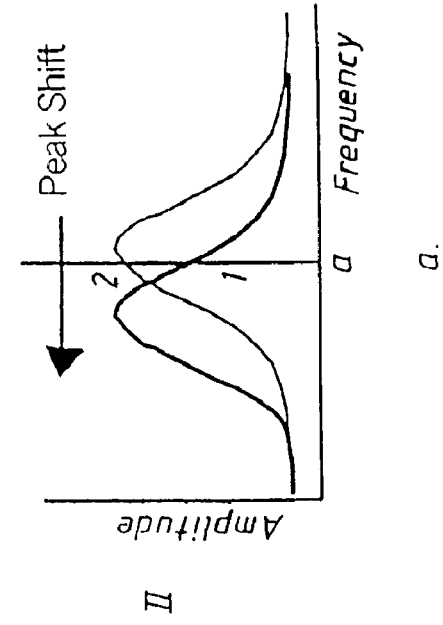
Fig. 8

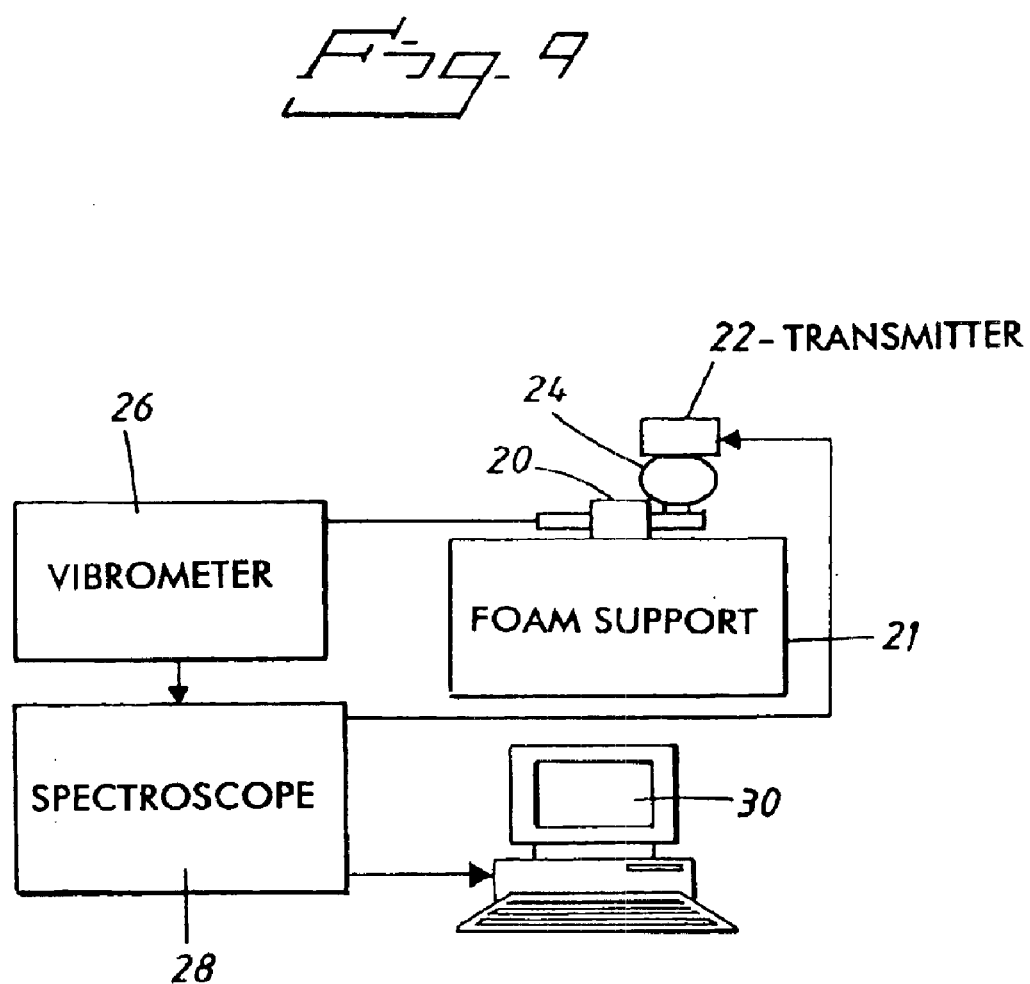

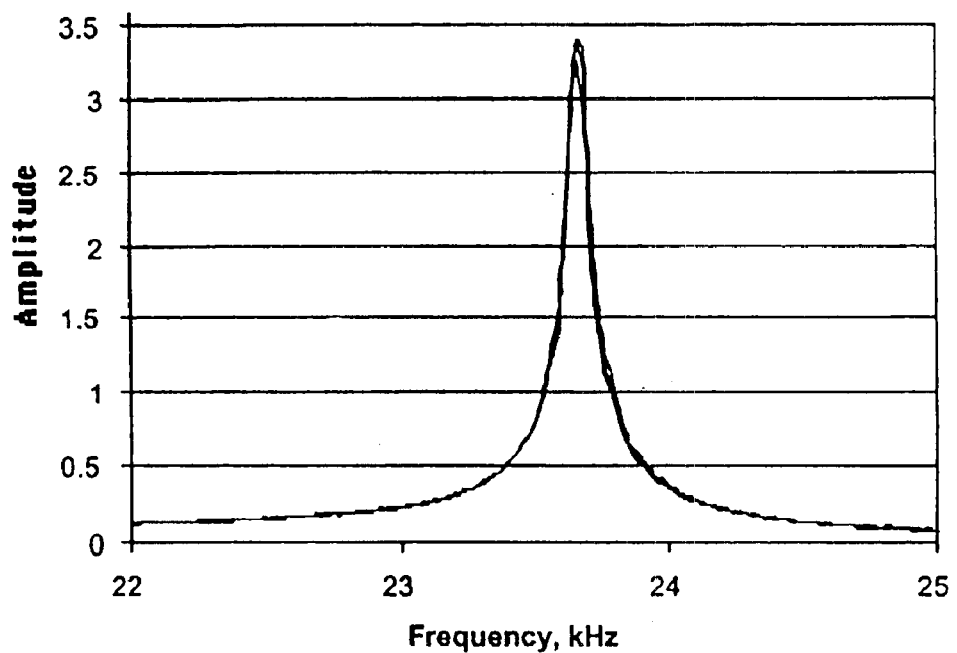
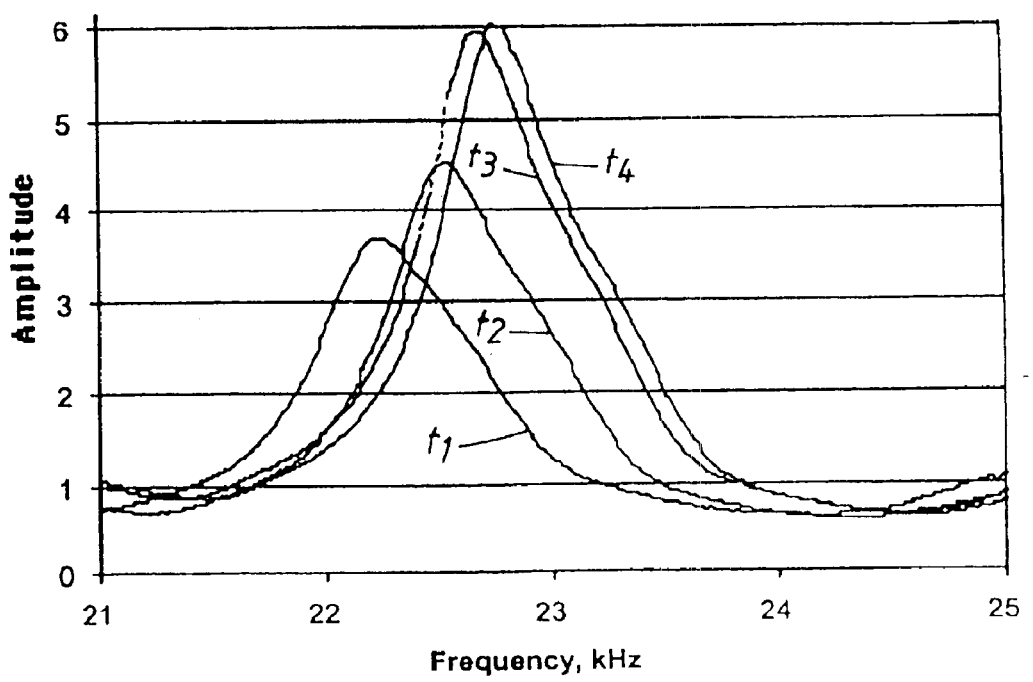

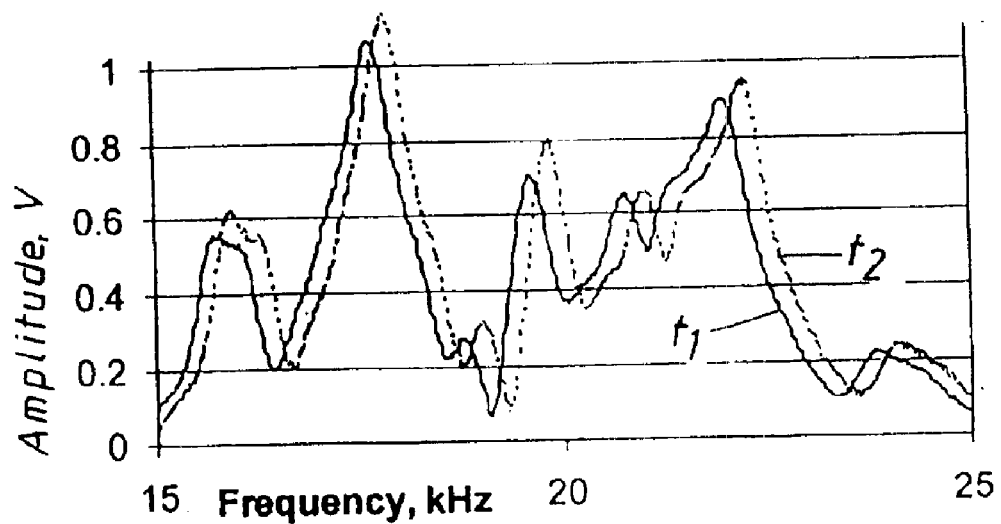
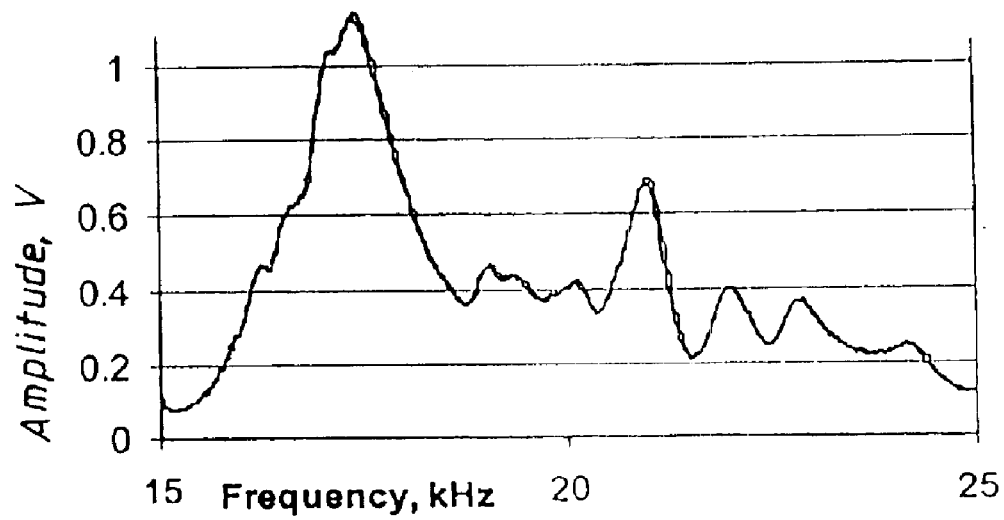

METHOD AND DEVICE FOR DETECTING DAMAGE IN MATERIALS OR OBJECTS

PRIORITY APPLICATION

This application is a U.S. National stage of PCT/SE02/00259, filed Feb. 14, 2002 and claims priority from Swedish Application No. 0100495-1, filed Apr. 2, 2001.

BACKGROUND OF THE INVENTION

The present invention relates to a method and a device for non-destructive detection of damage in materials or objects.

There are numerous acoustical techniques previously known for determining damage or defects in materials or objects.

In U.S. Pat. No. 5,086,775 a technique is thus described for estimating the spatial distribution of the vibration amplitude of an object. A low frequency vibration source is used to force the object to oscillate. The frequency of the vibration source is suitably chosen such that an eigenmode of the object is excited. Pulsed ultrasound is then transmitted to the object and by analysis of the Doppler shift of signals reflected by the object the vibration amplitude is determined. In this way abnormal regions in the object are detected due to different mechanical properties of these regions from those of normal regions which in its turn influence the vibration pattern. The described technique is primarily intended for detection of hard tumors surrounded by soft tissues.

In WO 9939194 a method and an apparatus for acoustic detection and location of defects in a structure or ice on the structure are described. A vibration signal of low frequency and a probe signal of a higher frequency are then supplied to the structure. In an undamaged structure these two signals propagate independently without any interaction. In a structure containing a defect, e.g. in the form of flaws, or with ice thereon, the vibration varies the contact area in the flaw or between ice and structure, which results in modulation of the high frequency probe signal. In the frequency domain this modulation manifests itself as frequency sidebands with respect to the frequency of the probe signal.

Thus U.S. Pat. No. 5,732,642 discloses a method and system to detect defects in a material wherein waves of known frequency(ies) are mixed at an interaction zone in the material. As a result, at least one of a difference wave and a sum wave are generated in the interaction zone. The difference wave occurs at a difference frequency and the sum wave occurs at a sum frequency. The amplitude of at least one non-linear signal based on the sum and/or difference waves is then measured. The non-linear signal is defined as the amplitude of one of the difference wave and sum wave relative to the product of the amplitude of the surface waves. The amplitude of the non-linear signal is an indication of defects (e.g., dislocation dipole density) in the interaction zone.

U.S. Pat. No. 5,520,052 discloses a method and apparatus for determining material structural integrity by combining laser vibrometry with damping analysis techniques to determine the damping loss factor of a material. The method comprises the steps of vibrating an area to be tested over a known frequency range and measuring vibrational force and velocity as a function of time over the known frequency range. Using known vibrational analysis, a plot of the drive point mobility of the material over the pre-selected frequency range is generated from the vibrational force and velocity measurements. Once computed, the damping loss factor can be compared with a reference sampling loss factor to evaluate the structural integrity of the material.

U.S. Pat. No. 5,214,960 discloses a method and apparatus for detecting defects in an object by vibrating the object in a plurality of positions. While the test object is vibrating, signals indicative of the vibration of the test object are detected and a signal indicative of a natural vibration of the test object is produced, as well as a signal indicative of a defect-induced vibration of the test object is produced. The signal indicative of the natural vibration and the signal indicative of the defect-induced vibration are compared to determine whether there is a defect in the test object.

U.S. Pat. No. 5,528,924 discloses an acoustic tool for analysis of a gaseous substance specifically a refrigerant gas, to determine whether the sample contains significant contaminants. The refrigerant is tested by introducing a vapour sample into a resonant chamber, which is formed to produce two distinct resonances, the resonator having first and second necks connecting first and second volumes. A frequency generator produces a sweep of frequencies in a band and then includes the two resonances and the sweep is applied to a transducer in one of the volumes. Another transducer responsive to vibrations produces an output signal that varies in response to the amplitude of the vibrations in the chamber. A digital circuit responsive to the frequency generator and the second transducer output determine the centre frequencies for the first and second resonances and determines the frequency width of these resonances to determine quality or sharpness factors for the two resonances. Then the centre frequencies and sharpness factors are compared with storage data and a determination as to the nature and extent of contaminants is made.

U.S. Pat. No. 5,425,272 discloses the use of relative resonant frequency shifts to detect cracks. At least two prominent resonant frequencies of an object are sensed and the frequency difference is measured. The ratio of the frequency difference to one of the prominent resonance frequencies is determined and compared to predetermined criteria. A resonance frequency dependent upon dimensions will shift very little while a resonance frequency dependent upon stiffness will shift a relatively large amount when an object has a crack.

U.S. Pat. No. 5,355,731 discloses a method for grading production quantities of spherical objects. A resonant ultrasound spectroscopy (RUS) spectrum is then generated from a spherical object. Sphere parameter values for the spherical object are determined from first components of the RUS spectrum. An asphericity value of the spherical object is determined from second components of the RUS spectrum and the spherical parameter values. The asphericity value is then compared with predetermined values to grade the spherical product.

U.S. Pat. No. 5,284,058 discloses a method for measuring complex shear or Young's modulus of a polymeric material wherein first and second beams of preselected lengths and different thickness are disposed in parallel spaced relationship firmly held at the ends thereof and first and second spaced gripping members are attached along the beams, a specimen of polymeric material is disposed between confronting surfaces of the gripping members, a time varying force is applied to one beam, the time varying displacements of the beams are measured, and the modulus of the polymeric material is calculated from the measurements.

U.S. Pat. No. 5,179,860 and U.S. Pat. No. 5,144,838 disclose a defect detecting method which includes the steps of vibrating the object, picking up the vibration, and detecting that a spectrum of the characteristic vibration of the object to be measured is separated into two portions. The method can also be used to detect cracks by vibrating an object, picking up the vibration, and detecting that an odd order spectrum of the characteristic vibration of the object to be measured is separated into two portions. A non-through defect can be determined in the same way by detecting that an even order spectrum of the characteristic vibration of the object to be measured is separated into two portions.

U.S. Pat. No. 4,944,185 discloses a method for non-destructively inspecting the integrity of a material by tagging the material, applying the material, activating the tagged particles to cause an inherent structural resonance in the tagged material, monitoring and measuring the structural resonance of the material with a probe, and relating the structure resonance of the material to the structural integrity of the material. This technique has particular application to adhesive materials.

U.S. Pat. No. 4,689,993 discloses a method and apparatus for measuring and mapping vibrations wherein one or more local sensors and a measuring means make local registrations and frequency decompositions of the vibrations of an oscillating object. The same sensors and measuring means can also be used with an image-forming unit and associated measuring means for local and image-forming recording of the vibrations of an oscillating object.

Further, in U.S. Pat. No. 3,958,450 a technique is described for determining surface properties, such as hardness, of materials by studying vibrations excited in the surface.

U.S. Pat. No. 5,216,921 describes a method and an apparatus for detecting defects and different hardness portions of an object with protrusions. Mechanical vibrations are then applied to the test object and by spectral analysis of data about how the different protrusions are vibrating defects and/or different hardness portions are determined in each of the protrusions.

U.S. Pat. No. 5,777,891 discloses an ultrasonic technique for real-time detection of flaws. A plurality of ultrasonic impulses are then injected to the material and echoes caused by discontinuities in the material are analysed regarding signal amplitude, travel time and spreads are compared with corresponding values of pattern for known discontinuities in the material for localising flaws. The described technique is primarily intended for use on rails, and in particular for separating true flaws from intervals between rails in rail junctions.

U.S. Pat. No. 6,023,980 finally, deals with the study of fatigue in materials. A test machine is described used for then applying static and dynamic stress loadings with frequencies in the range of 1000–4000 Hz.

A new physical phenomena in solid material, named "slow dynamics", has recently been discovered, see Robert A. Guyer and Paul A. Johnson, "Non-linear Mesoscopic Elasticity: Evidence for a New Class of Materials", Physics Today, April 1999, pp. 30–36. Slow dynamics is a transient or temporary change in the elastic modulus of damaged materials, related to non-linearities due to the presence of cracks in such damaged materials.

SUMMARY OF THE INVENTION

The purpose of the present invention is to propose a robust, quick and sensitive non-destructive technique for detection of damage in materials and objects, based on this new physical phenomena slow dynamics.

This purpose is obtained by a method and a device according to claims 1 and 23 respectively.

Thus with the present invention a method and a device for non-destructive detection of damage in materials or objects are provided which are well adapted to be automated for application to e.g. production lines. The technique according to the invention is well suited for detection of progressive fatigue damage in objects, portions of structures, and possibly in entire structures. The technique is also well suited for monitoring in line production for quality assurance and can be applied to tests for damage in materials in general, e.g. in aircraft and spacecraft components, automotive components, etc.

The present invention is based on measurements of slow dynamics induced material elastic modulus changes appearing when physically influencing a damaged material or object. An undamaged material or object shows no slow dynamic response, whereas a damaged material or object shows a large slow dynamic response. This effect can be explained as follows. The physical influence produces two different physical states in damaged material, one more rigid and one less rigid. The less rigid state is transient and induced by the physical influence because of the presence of damage. Shortly after excitation of slow dynamics by the physical influence on the material, the material returns to its more rigid state. When probing the material, two different material states, viz, one rigid (the material state before excitation) and one less rigid (the material state immediately after excitation) are detected. This temporary change of state is used as an indication of damages, like cracks, in the material.

Thus a crack or other crack-like defect in a sample, like a material or object, changes the physical properties of the material. The appearance of slow dynamics is consequently an important, previously unknown change in the physical properties. According to the present invention tests devised to interrogate the existence of slow dynamics in a sample provide information whether damage is present or not. In this way slow dynamics can be used for damage or crack detection.

When a damaged material is physically influenced such as by, but not exclusively, a mechanical impact, an electromagnetic impulse, a continuous wave driving source, a change in temperature, a change in applied load such as an ambient pressure change, the material elastic modulus will change. Any physical change that induces slow dynamics can be used in this connection.

There are numerous manners to observe slow dynamics as will be described below.

The present invention is based on measurements of slow dynamics induced elastic modulus changes appearing when physically influencing a damaged material as indicated above. An undamaged material or object shows no slow dynamic response, whereas a damaged material or object shows a large slow dynamic response. This effect can be explained as follows. The physical influence produces two different physical states in damaged material, one more rigid and one less rigid. The less rigid state is transient and induced by the physical influence because of the presence of damage. Shortly after the material is excited by the physical influence the material returns to its more rigid state. When probing the material, two different material states, viz, one rigid (the materials state before excitation) and one less rigid (the materials state immediately after excitation) are detected. This temporary change of state is used as an indication of damage, like cracks.

According to an advantageous embodiment of the method according to the invention a sweep signal is supplied to the material or object, the frequency of this sweep signal is varied over a predetermined frequency interval to determine eigenmodes of the material or object, a probe signal of at least one tone of a single frequency chosen to be situated in a selected point on a resonance peak corresponding to a selected one of said determined eigenmodes is supplied to the material or object, said probe signal is sensed in the material or object while physically influencing the material or object, and the effect of said physical influence on said probe signal is sensed to detect said changes in the material or object elastic modulus.

According to other advantageous embodiments of the method according to the invention the frequency of the probe signal is chosen to be positioned on one flank of the eigenmode resonance peak, and preferably on or near the inflection point of the flank. Even if it is possible to position the probe signal frequency on top of the peak itself, it is an optimum choice of probe signal frequency to position it on a peak flank and especially in or near the inflection point, resulting in a maximum sensitivity. This is a very important feature of the invention which is called 'slope amplifier' or 'eigenmode differential amplifier' and which increases the signal-to-noise ratio of the measurements by at least a factor of 10 over any other method involving slow dynamics or non-linear wave mixing.

According to still other advantageous embodiments of the method according to the invention the material or object is excited with a large amplitude, broad frequency band signal of, preferably 10–1000 times, larger amplitude than the probe signal. The large amplitude signal can alternatively be a single tone signal and be a continuous signal. The large amplitude signal excites the slow dynamics of the material and temporarily changes resonance modal frequencies. This change in modal frequencies dramatically affects the amplitude of the pure tone probe signal if the material or object is cracked or flawed, and this large change in amplitude due to flaw or crack induced slow dynamics can be easily detected.

According to yet another advantageous embodiment of the method according to the invention for use on a production or manufacturing line changes in the monitored amplitude of the probe signal are compared to predetermined baseline information to determine pass or fail status for the material or object. Such baseline information must be determined by other methods in advance to know what is acceptable and what is not acceptable to the component in question. Once the limit for acceptability is determined and the slow dynamical response is calibrated to the limit of acceptability, the method according to the invention can be used to infer pass/fail and be applied to large quantities of samples on a production or manufacturing line.

According to advantageous embodiments of the device according to the invention the second signal generator for supplying a probe signal is connected to an acoustic signal source, such as a piezoelectric transducer, to be contacted with the material or object for supply of the probe signal, or connected to a non-contact wave source, such as a speaker, for contactless supply of the probe signal to the material or object. Thus the probe signal can be transferred to the material or object by a direct contact or contactless depending on the application in question.

The first signal generator, for obtaining the eigenmode frequencies, and second signal generator, for providing the pure tone probe frequency, can be two separate signal generators. In this case the second signal generator can be of a cheaper type since this generator is producing a signal of a constant frequency.

According to an advantageous embodiment of the device according to the invention said first and second signal generators can, as well, be one and the same signal generator.

According to still other advantageous embodiments of the invention said large amplitude signal source for physically influencing the material or object comprises either a broad frequency band source, such as a laser impulse source or a mechanical hammer intended to strike the material or object to be investigated, or a continuous wave source such as a speaker or a piezoelectric transducer. The large amplitude signal source in this way induces the material or object to ring. Both these sources are large amplitude sources suitable for this use. However, also other sources may be suitable as well. The actual choice of source is dependent on the application in question.

According to yet other advantageous embodiments of the device according to the invention the data acquisition system comprises a digitising means for collecting the output signal (s) from the material or object. This digitising means can comprise a digitiser of acceptable frequency and amplitude bandwidth, like an oscilloscope or a digitising board in the computer.

According to another advantageous embodiment of the device according to the invention at least one vibration sensor is provided to contact the material or object to deliver said sensed output signal to said data acquisition system. Normally one sensor will be enough for this purpose. However, in some cases, depending on the location of the damage, detection of damage can then be missed. The risk of such a miss is however low. Anyhow this risk can be practically totally eliminated by using separate sensors on the material or object in question and/or by using another one of the modes, belonging to specific frequencies, of the material or object, that is, by use of a frequency close to another resonance mode. There exist two ways to miss a damage. Either the damage can be in a location which is weakly excited by the mode belonging to the specific frequency, or the detector is in a place weakly excited by the mode belonging to the specific frequency.

According to yet another advantageous embodiment of the device according to the invention at least one vibration sensor comprises a non-contact wave detector to sense and deliver said sensed output signal to said data acquisition system. A non-contact laser or acoustic vibrometer are examples of such a non-contact detector, which can be highly advantageous for some applications.

According to still another advantageous embodiment of the device according to the invention a high pass filter is provided to filter away frequency components of said sensed signal well below the frequency of said probe signal. The components of the output signals of highest amplitude are normally low frequency resonance components generated by the large amplitude signal source. The signal frequency of interest is, however, the pure tone probe signal frequency, which normally has considerably higher frequency. In order to eliminate the influence from the low frequency resonances induced by the large amplitude signal source a high pass filter is used.

BRIEF DESCRIPTION OF THE DRAWINGS

The invention will now be described in greater detail with reference to the accompanying drawings, on which FIGS. 2–7 show different examples of output signals picked up from test materials or objects, FIG. 8 shows examples of output signals as a function of time together with examples of associated eigenmode frequency curves FIG. 9 shows schematically a second embodiment of the device according to the invention, FIGS. 10–11 measured amplitude frequency responses as a function of time for an undamaged and a damaged object, FIGS. 17–20 show amplitude frequency responses measured on damaged and undamaged objects with alternative embodiments of the invention.

FIG. 1 shows a block diagram of an exemplifying embodiment of the device according to the invention. The frequency of a signal generator 2 is swept across a predetermined, large frequency interval for determining resonance modes (eigenmodes) of the material or object 4 to be investigated. The sweeping of the frequency is controlled by a computer 6. The signal from the signal generator 2 is amplified in an amplifier 8 and supplied to the material or object 4 by a transducer 10.

Figure 1:
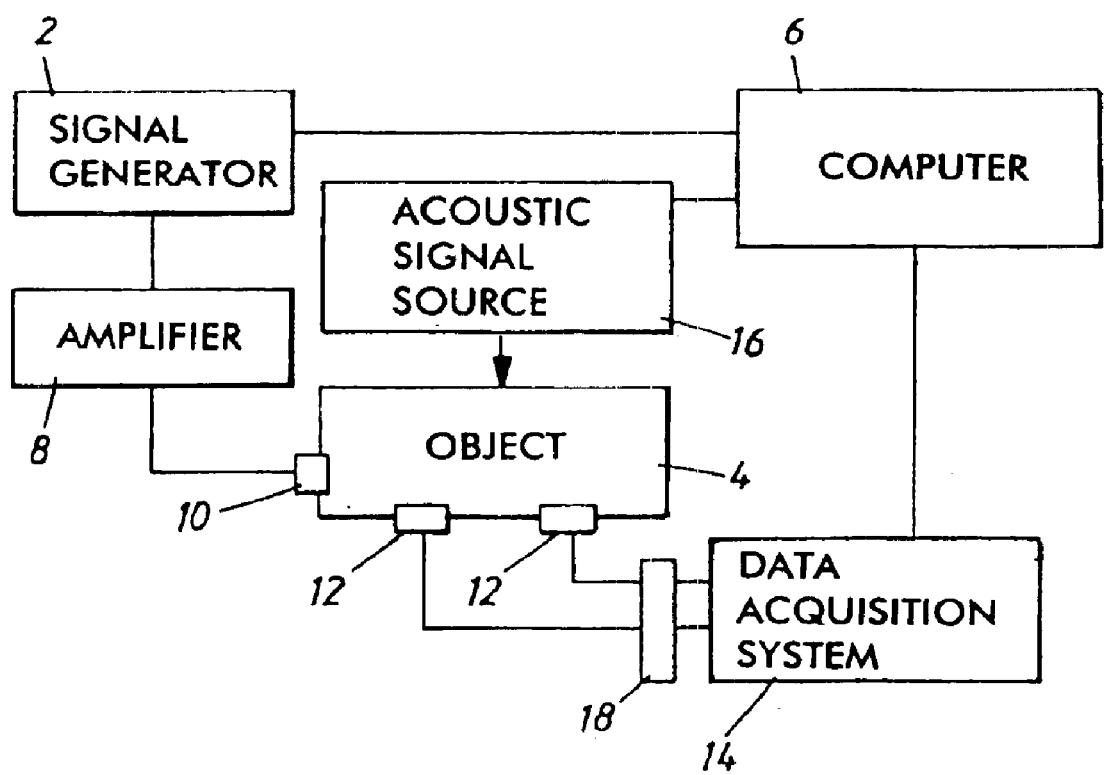
FIG. 1 is a block diagram illustrating the principal layout of a first embodiment of the device according to the invention.

Ultrasonic and vibration sensors 12 are provided to detect output signals from the material or object 4 for delivering these output signals to a data acquisition system 14. The data acquisition system 14 comprises a digitising device which can be any digitiser of acceptable frequency and amplitude band width and it can be contained inside the computer, e.g. in the form of a digitising board, or be located external to the computer, e.g. in the form of a digital oscilloscope.

The acoustic source, which inputs a single tone probe signal or a probe signal of a group of single tones can be in direct contact with the material or object 4 by way of a suitable contact device, such as a piezoelectric transducer, or the probe signal can be transferred to the material or object 4 by a contactless device such a as a loudspeaker. As mentioned above the signal generator 2 can be used as this acoustic source.

A large amplitude acoustic signal source 16 is provided to physically influence and excite slow dynamics in the material or object 4 by a large amplitude wave or signal. This large amplitude acoustic signal source can include a laser delivering laser pulses, a mechanical hammer, or some other appropriate device. The signal source can be a broad frequency band signal, a signal of moderate frequency band width, or a single frequency tone signal. The large amplitude signal can also be continuous signal.

In the embodiment shown in FIG. 1 two sensors 12 are shown. Normally one sensor is sufficient. However, when using only one sensor there is a (small) risk that a damage can be missed, depending on where the damage is located in the material or object 4, where the transducer 10 is positioned and where the sensor is situated. If the sensor has been given an inappropriate location for the prevailing situation, damage can be missed.

The first step of the technique according to the invention consists in a study for determination on the linear eigenmodes (the resonance modes) of the test sample, in the form of the material or object 4. This is performed by sweeping the frequency of the signal, supplied by the signal generator 2, to the sample 4, and measuring the output time averaged amplitude, by sensors 12, data acquisition system 14 and possible the computer 6. This step is a kind of resonance ultrasound spectroscopy.

From the gained information about the eigenmodes a pure tone frequency is selected on one of the flanks of a resonance peak (eigenmode), and the signal generator 2 is controlled from the computer 6 to produce a continuous output wave at this pure tone frequency. This signal is amplified, by amplifier 8, and supplied to the test material or object 4 as a probe signal. This signal can be supplied to the test material or object 4 in different ways, depending on the actual application. In the embodiment shown in FIG. 1 this is performed by way of a transducer 10.

While the continuous probe signal is supplied to the test material or object 4, a large amplitude signal is input to the test material or object 4 from the acoustic source 16. This signal source must be repeatable. Different kinds of signal sources can be used for this purpose, e.g. a calibrated mechanical hammer, or a laser delivering laser pulses, for example.

Thus by this acoustic source 16 the test material or object 4 is impacted to excite slow dynamics which temporarily will change the resonance mode frequencies. The change in resonance mode frequencies drastically affects the amplitude of the pure tone probe signal if the sample 4 is damaged, e.g. is cracked or flawed, and this large change in amplitude due to e.g. flaw induced slow dynamics is utilised for indicating such damage.

A suitable triggering means is provided to trigger the digitiser of the data acquisition system 14 from the large amplitude acoustic signal source 16 such that the operation of the data acquisition system is correlated to the operation of this acoustic source 16. It is very important that the record and analysis of the sensed signal is synchronised to the impact of the material or object by the large amplitude signal such that this record and analysis starts just after impact.

When the acoustic impact source 16 strikes the test material or object 4, the resulting output signal, sensed by the sensors 12, is fed through a high pass filter 18 to the digitiser, e.g. an oscilloscope, of the data acquisition system 14. The signals of highest amplitude sensed by the sensor 12 are normally low frequency eigenmodal signals generated by the acoustic impact device 16. The signal of interest is, however, the pure tone, continuous probe signal which normally has a considerably higher frequency. To eliminate the influence of the low frequency signal components induced by the broad band impact signal source 16 a high pass filter 18 is therefore used. As an example, the signal generator 2 may produce a continuous probe signal of 180 kHz. The acoustic impact source 16 can induce a high amplitude response from the test material or object 4 in the frequency band from near DC to about 10 kHz, where signal dissipation effects are lower. The high pass filter 18 will pass all frequencies above e.g. 15 kHz. Of course these figures are just examples and may be changed depending on test sample and application.

When the large amplitude signal source 16 strikes the object, a high pass filtered time signal is sensed by the sensors 12 and supplied to the digitising means of the data acquisition system 14. This signal contains the information required to infer whether or not damage exist in the test sample 4. From this signal a relatively quantitative yes/no (pass/fail) result for the test material or object 4 can be obtained quickly and easily by inspecting, processing and analysing the sensed output signal. Suitable means therefor, like comparator means for determining the sensed signal with predetermined baseline information, are included in the data acquisition system 14 or in the computer 6 in the embodiment shown in FIG. 1.

The first portion of the signal shown in FIG. 2 is the continues probe signal input. In this example the frequency of the probe signal is about 193 kHz. At time zero in the figure the test sample is struck by an impact source in the form of a hammer. In this case this test sample is an automotive alternating housing. The change in the amplitude after time zero indicates that damage is present in the test object.

FIG. 3 shows the received signal from an identical undamaged alternating housing. In this undamaged sample no change is observed in the signal amplitude after the impact of the sample.

FIG. 4 shows the sensed signal as the function of time for a damaged automotive engine bearing cap. In this case the frequency of the used probe signal is 180 kHz. The decrease in amplitude after the impact on the sample, at time zero, indicates that the bearing cap is damaged.

FIG. 5 shows another example of the sensed signal as a function of time from an automotive engine bearing cap using a different probe signal frequency than in FIG. 4, viz. 181 kHz. The increase in the probe signal amplitude at the time of the impact, time zero, indicates that this sample is damaged.

FIG. 6 shows the sensed signal as a function of time for a polycarbonate sample made from material used for aircraft canopy. The change in the probe signal amplitude after time zero, i.e. after impacting the test object, indicates the presence of a damage in the test object. In this example frequency of the probe signal is 198 kHz.

FIG. 7 shows the sensed signal as a function of time for a steel pipeline containing a surface stress corrosion crack. Also in this case the change in the probe signal amplitude after time zero, i.e. after impacting the test object, indicates the presence of a damage in the test object. In this case the frequency of the probe signal is 204 kHz.

The observed slow dynamical induced amplitude change in the damaged test samples can be explained as follows.

A modal resonance peak as shown in diagrams II in FIG. 8, will move to lower frequency for a certain time, when the sample is impacted by a large amplitude signal source, cf. curve 2 in diagrams II in FIG. 8. This is the phenomenon of slow dynamical material softening. Most of the softening, and the corresponding resonance peak shift, exist only as long as the large amplitudes from the impact exist in the sample.

In FIG. 8 the diagrams I show a probe signal as a function of time before 1 and after 2 the effect of the large amplitude impact source. Diagrams II illustrate an arbitrary eigenmode with the frequency of the probe signal indicated by a vertical line a. A continuous probe signal is input into the sample at 1 in the diagrams I. When the sample is impacted by the large amplitude signal source, at 2 in diagrams I, the mode shifts as shown by the arrow and bold curve in diagrams II, and the probe signal amplitude changes accordingly, cf. diagrams I in FIG. 8. After a period of time the probe signal amplitude returns to its original value 1.

Diagrams a in FIG. 8 show an example wherein the probe signal amplitude decreases as a function of the resonance mode shift and diagrams b shows an example where the probe signal amplitude increases as a result of such a mode shift. The change of the amplitude of the probe signal will depend on the input volume and the relative location of the eigenmode peak. On impact of the test sample the resonance peak moves leftward to the location illustrated by the bold line, position 2 in diagrams II in FIG. 8. As it appears the net amplitude change of the probe signal depends on the proximity of the frequency of the probe signal to the resonance peak, after a comparatively short time the test sample returns to its original state and the amplitude of the probe signal returns to its original amplitude 1. As a matter of fact slow dynamics induced by the impact make the recovery of the test sample take tens of minutes, however, most of the amplitude is recovered very quickly, which also make the detecting technique according to the invention quick.

As mentioned above FIG. 8a shows an example in which the amplitude of the probe signal increases whereas FIG. 8b illustrates a situation in which the amplitude decreases. This depends on different locations of the probe signal frequency in relation to the eigenmode. The probe signal amplitude can also remain substantially constant if the frequency of the probe signal should happen to be located on or near the resonance peak or in a frequency band where no eigenmodes exist. In this situation, after having ended up with the wrong choice of frequency resulting from not following the correct procedure, the technique according to the invention fails. An optimum location of the probe signal frequency is at the inflection point of the eigenmodes. This is a very important feature of the invention and the reason why a frequency sweep is conducted first such that an optimum frequency can be selected for the probe signal.

The above-described effect on which the invention is based appears only in damaged material, either locally damaged, e.g. a cracked sample, or volumetrically damaged, e.g. a sintered metal component. For undamaged samples unaffected signals as shown in FIG. 5 are obtained. Thus, if slow dynamical amplitude changes occur in the continuous probe signal this indicates that the test material or object is damaged.

Thus, to sum up, the large amplitude impact source is producing two different physical states in the cracked test material or object, one more rigid state and one less rigid. The less rigid state is transient and induced by the large amplitude signal source. Shortly after the impact from the large amplitude signal source the material or object returns to its more rigid state. When the material or object is probed with a high frequency probe signal during excitation by the broad impact source, the continuous probe signal samples two different material states, one rigid state before the impact and one less rigid state at or shortly after the impact. This means that the high frequency probe signal will change in amplitude temporarily. This creates a signal in the time domain which can be sensed and which changes in amplitude as shown in the figures and explained above due to the presence of cracks or other damage in the material or object.

In exceptional cases the above described embodiment of the invention can fail if the eigenmode selected for probing with the pure-tone does not "sample" the damaged region. This could happen in very complex objects. Using of multiple simultaneous tones at different eigenmodes will eliminate this problem. This simply means that in the case of geometrically very complicated objects it will take more time to carry out the method according to the invention.

FIG. 9 illustrates schematically a second embodiment of the device according to the invention for detecting slow dynamics from transient frequency displacement of eigenmodes. A continuous acoustic ultrasonic wave is supplied to a test object 20 in the form of a powdered metal ring resting on a foam support 21. The acoustic wave is transferred from a piezoceramic transmitter 22 through a rubber bladder 24 filled with water. The signal in the object 20 is measured by a laser vibrometer 26 and analysed and processed in a resonant ultrasound spectroscope 28 and a computer 30.

Figure 12:
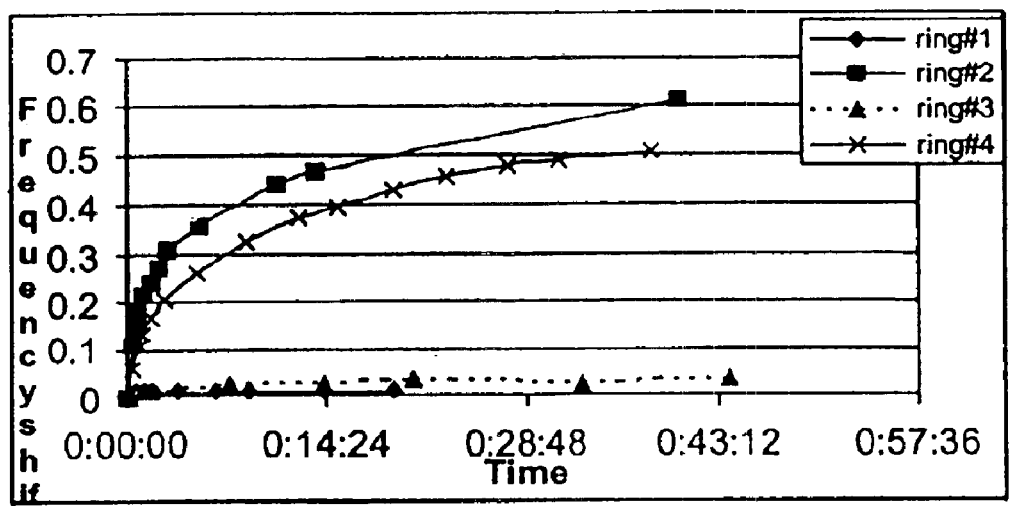
FIG. 12 shows the resonance frequency shift as a function of time measured on four different objects.

FIGS. 10–12 show measured amplitude frequency responses for undamaged and a damaged rings, excited by an air gun, as well as measured resonance frequency shift as a function of time. Thus FIG. 10 shows the amplitude frequency response in the frequency band 22–25 kHz for an undamaged object measured at four different times after the excitation of the object. This figure shows no frequency shift but the four measured resonance curves coincide.

FIG. 11 shows correspondingly amplitude frequency responses measured on a damaged object. In this case after excitation a clear frequency shift of the measured resonance curve is observed. It can also be noted that the amplitude frequency response gradually returns towards its "non-excited" position with increasing time after excitation of the object, Thus the curve marked with $t_1$ is measured at time $t_1=10$ sec after excitation of the object, the curve marked with $t_2$ is measured at $t_2=5$ min and 9 sec after excitation, curve $t_3$ after a time $t_3=19$ min and 14 sec after excitation, and curve $t_4$ after $t_4=38$ min and 16 sec after excitation of the object.

FIG. 12 shows resonance frequency shift as a function of time measured with a device according to the invention on four different metal powder rings. These measurements obviously show that rings 2 and 4 are damaged whereas rings 1 and 3 are undamaged.

Figure 13:
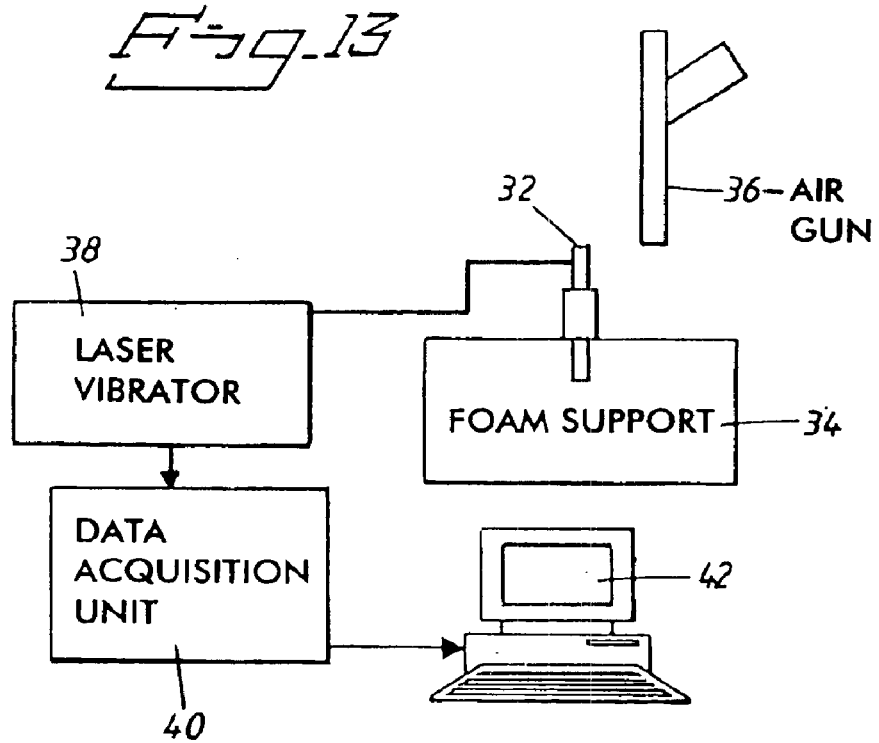
FIG. 13 shows schematically a third embodiment of the device according to the invention.

A third embodiment of the device according to the invention is schematically illustrated in FIG. 13. A test object 32 is resting on a foam support 34. An air gun 36 is used to excite slow dynamics in damaged samples of the object 32. A supplied probe signal is sensed in the object 32 by a laser vibrator 38. The sensed signal is transformed to digital format in the data acquisition unit 40 and processed in the computer 42.

Figure 14:
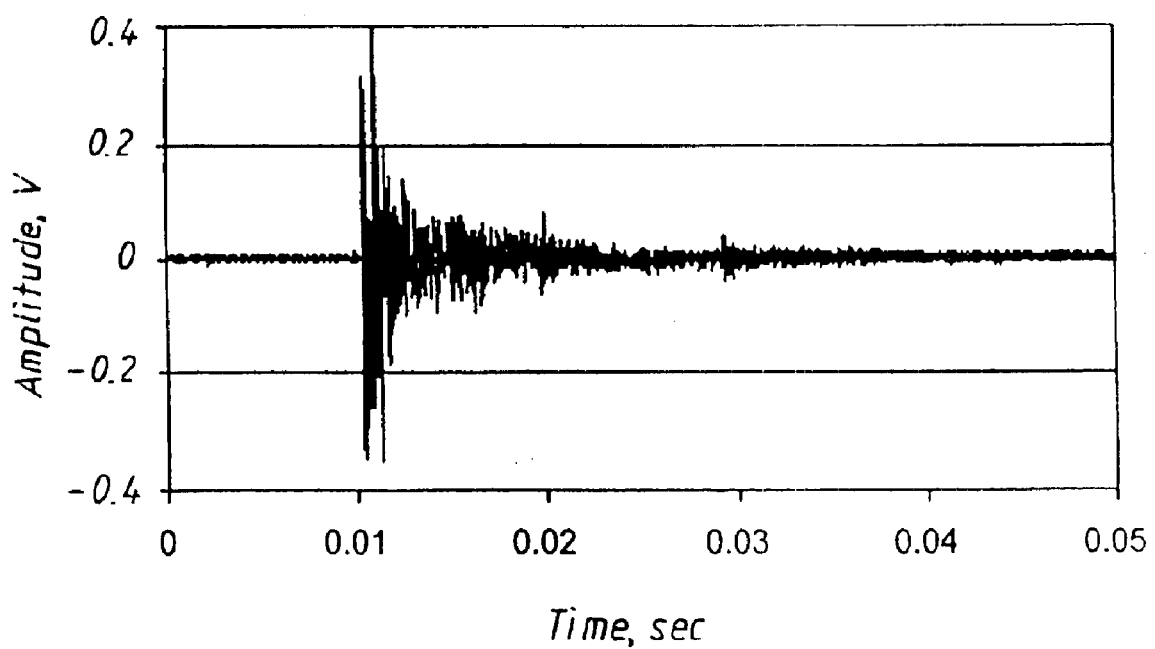
FIG. 14 shows another example of the amplitude as a function of time measured on a damaged object after excitation of the object.

The measured amplitude as a function of time for a damaged object is shown in FIG. 14, excitation of the object taking place at about time 0.01.

Figure 15:
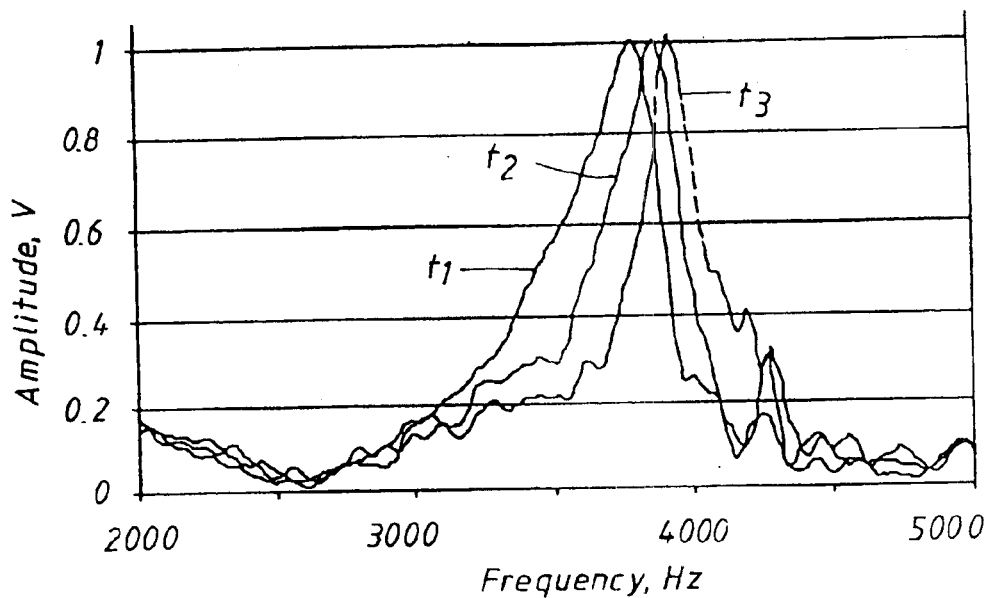
FIG. 15 shows another example of measured amplitude frequency responses as a function of time for a damaged object.

FIG. 15 is a diagram corresponding to that of FIG. 11 showing resonance frequency response curves during the recovery period of a damaged object, measured at $t_1=35$ sec after excitation of the object, at $t_2=2$ min and 10 sec after excitation and at $t_3=7$ min and 30 sec after excitation. In this example sensing means in the form of a non-contact sensor is used.

Figure 16:
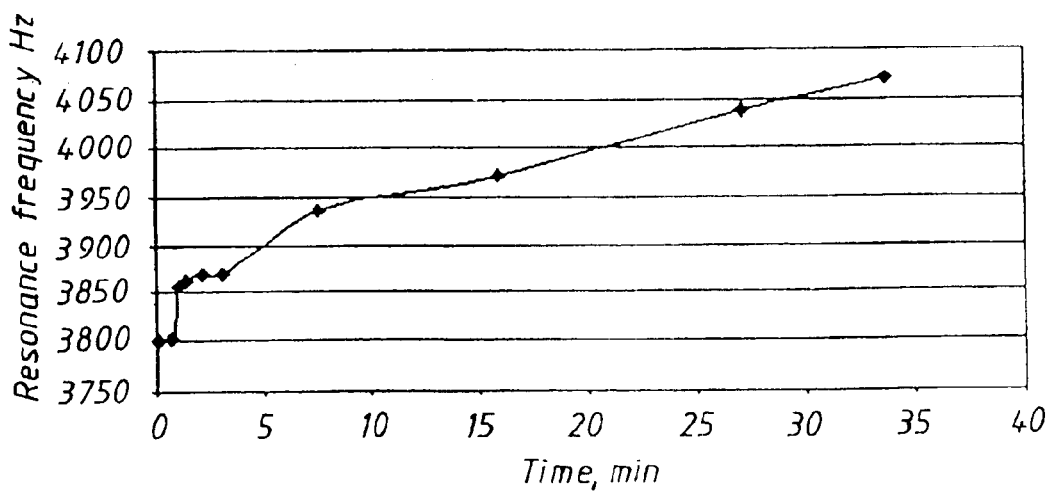
FIG. 16 illustrates the resonance frequency shift as a function of time measured on a damaged object.

FIG. 16 is a diagram qualitatively corresponding to that of FIG. 12 showing measured resonance frequency of an eigenmode as a function of time after excitation of a damaged object in the form of a ring.

FIGS. 17–20 show amplitude frequency responses measured by a device according to the invention by sweeping the signal over the frequency range 15–25 kHz. As appears from these figures this frequency range contains several eigenmodes. FIG. 17 shows the amplitude frequency response obtained from an object in the form of a damaged ring of powered metal, excited by loading with a static weight of 2 kg. Curve $t_1$ is measured immediately after the release of the exciting load and curve $t_2$ at time $t_2=30$ sec later. A clear frequency shift is observed which indicates a damaged object.

FIG. 18 shows results from similar measurement on another ring. No frequency shift is observed, thus indicating that this ring is undamaged.

Figure 19:
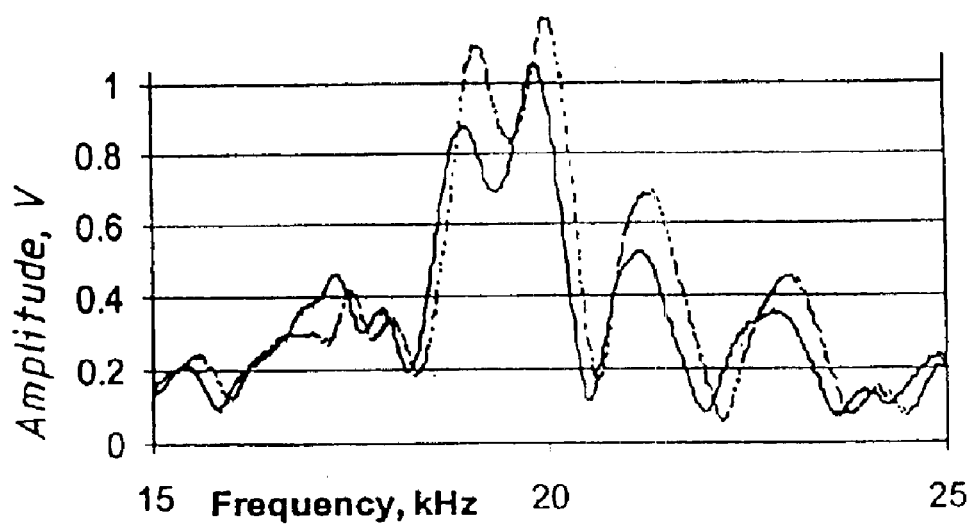
Figure 20:
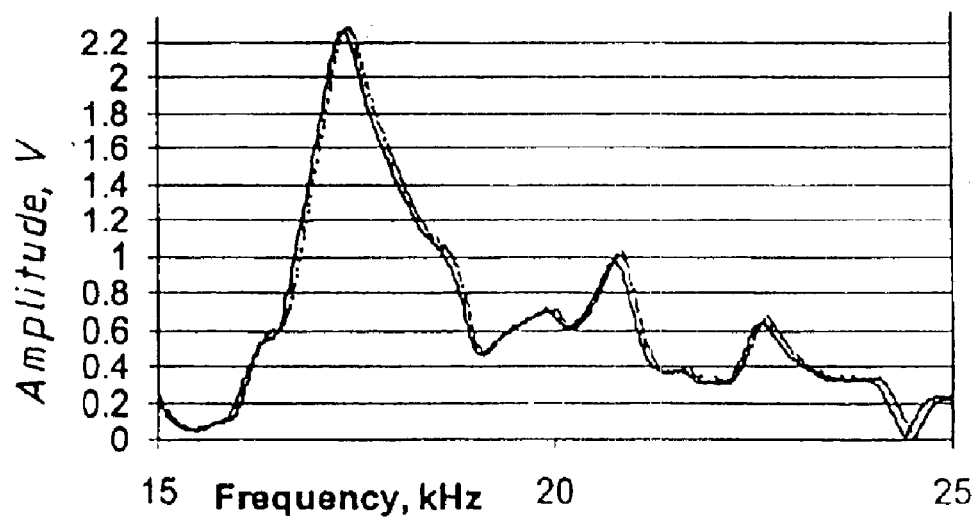

FIGS. 19 and 20 show the results of corresponding measurements as in FIGS. 17 and 18. However, in this case excitation or physical influence of the rings is provided by heating them by a contact iron during 5 sec. In FIG. 19 a clear frequency shift is noted between curves measured at different times after excitation, indicating a damaged ring. No such frequency shift is noted in FIG. 20, thus indicating an undamaged ring.

What is claimed is:

1. A method of detecting damage in materials or objects, wherein the material or object is physically influenced to produce a physical change of the material or object in case of damages therein, the method comprising influencing the material or object to induce transient slow dynamics in case of damage in the material or object;

detecting slow dynamics induced material elastic modulus changes by applying a probe signal to the material or object;

sweeping the frequency of the probe signal at least twice, before and after physically influencing the material or object, to determine at least one eigenmode of the material or object;

sensing the probe signal in the material or object while physically influencing it; analyzing the sensed signal to determine a transient frequency displacement of the eigenmode as an indication of a material modulus change resulting from a damage in the material or object.

2. The method according to claim 1, wherein physically influencing the material or object comprises impacting the material or object by applying an electromagnetic impulse to it.

3. The method according to claim 1, wherein physically influencing the material or object comprises impacting the material or object by applying a continuous electromagnetic wave to it.

4. The method according to claim 1, wherein physically influencing the material or object comprises impacting the material or object mechanically.

5. The method according to claim 4, wherein impacting the material or object comprises changing an applied load.

6. The method according to claim 5, wherein physically influencing the material or object comprises hitting the material or object by a mechanical hammer.

7. The method according to claim 1, wherein physically influencing the material or object comprises impacting the material or object by a change of temperature.

8. The method according to claim 1, wherein physically influencing the material or object comprises impacting the material or object by a change of the ambient pressure.

9. The method according to claim 8, wherein physically influencing the material or object comprises impacting the material or object by an air gun for providing an acoustic impulse.

10. The method according to claim 1, further comprising after determining eigenmodes of the material or object, supplying a probe signal to the material or object of at least one tone of a single frequency chosen to be situated in a selected point on a resonance peak corresponding to a selected one of the determined eigenmodes;

sensing the probe signal in the material or object while physically influencing the material or object; and analyzing the effect of the physical influence on the sensed probe signal to detect the changes in the material or object elastic modulus.

11. The method according to claim 10, wherein the selected point is chosen to be positioned on one flank of the eigenmode resonance peak.

12. The method according to claim 11, wherein the selected point is chosen to be located on or near the inflection point of the flank.

13. The method according to claim 10, wherein determining the eigenmodes, comprises sweeping the signal frequency over the predetermined frequency interval and increasing a time-averaged response from the material or object.

14. The method according to claim 10, wherein the electromagnetic wave to impact the material or object is a large amplitude signal with a broad frequency band signal of 10–1000 times, larger amplitude than the probe signal.

15. The method according to claim 10, wherein an electromagnetic wave impacts the material or object and is a large amplitude signal of a single frequency tone.

16. The method according to claim 14 wherein the frequency of the probe signal is considerably higher than frequencies of the large amplitude signal.

17. The method according to claim 14, wherein the probe signal is continuously supplied with constant amplitude.

18. The method according to claim 15, wherein the probe signal and said large amplitude signal are acoustic signals.

19. The method according to claim 10, further comprising supplying a plurality of single tone probe signals to the material or object, the signals having single tone frequencies chosen to be situated on different flanks of resonance peaks corresponding to selected ones of the determined eigenmodes, and monitoring the effect of the physical influence on the plurality of probe signals for detecting damages.

20. The method according to claim 10, further comprising monitoring changes in the monitored material or object elastic modulus and comparing them to predetermined baseline information to determine pass or fail status for the material or object for use on a production of manufacturing line.

21. A device for non-destructive detection of damage in materials or objects, comprising
    an impact source provided to impact the material or object to physically influence the material or object to produce a physical change of the material or object wherein the impact source is adapted to produce a physical change of the material or object to induce transient slow dynamics in case of damage therein;
    a probe signal source to supply a probe signal to the material or object;
    sweeping means to sweep the probe signal frequency at least twice, before and after physically influencing the material or object, to determine at least one eigenmode of the material or object;
    a sensor to sense the probe signal in the material or object while physically influencing it;
    an analyzer to determine a transient frequency displacement of the eigenmode as an indication of a material elastic modulus change resulting from a damage in the material or object.

22. The device according to claim 21 wherein the impact source comprises a signal generator adapted to impact the material or object with a continuous or pulsed electromagnetic wave for physically influencing the material or object.

23. The device according to claim 21 wherein the impact source comprises an air gun adapted to impact the material or object by an acoustic impulse for physically influencing it.

24. The device according to claim 21, further comprising a first signal generator for supplying a first signal to the material or object;
    a controller means to control the first signal generator to sweep the frequency of the first signal over a predetermined frequency interval;
    a determining device to determine eigenmodes of the material or object when sweeping the frequency of the supplied first signal;
    a second signal generator for supplying a probe signal of at least one single tone frequency to the material or object, the frequency being chosen to be situated in a selected point on a resonance peak corresponding to a selected one of the eigenmodes;
    a sensor to sense the probe signal in the material or object while physically influencing the material or object; and
    an analyzer to analyse the effect of the physical influence on the sensed probe signal for detecting changes in the material or object elastic modulus.

25. The device according to claim 24, wherein the selected point is positioned on one flank of the eigenmode resonance peak.

26. The device according to claim 24 further comprising a computer to form the controller.

27. The device according to claim 24, wherein the second signal generator is adapted to supply an acoustic probe signal.

28. The device according to claim 24, wherein the second signal generator is connected to an acoustic signal source as a piezoelectric transducer, to be contacted with the material or object for supply of the probe signal.

29. The device according to claim 24, wherein the second signal generator is connected to a non-contact wave source, for contactless supply of the probe signal to the material or object.

30. The device according to claim 24, wherein the second signal generator is adapted to supply a probe signal having a plurality of single tone frequencies.

31. The device according to claim 24, wherein the first and second signal generators are the same signal generator.

32. The device according to claim 23, wherein the impact source comprises a laser impulse source.

33. The device according to claim 23, wherein the analysing comprises a data acquisition system for receiving and analyzer sensed signals from the material or object.

34. The device according to claim 33, wherein the data acquisition system comprises a digitising means.

35. The device according to claim 33, further comprising at least one vibration sensor to contact the material or object to deliver the sensed signal to the data acquisition system.

36. The device according to claim 28, wherein the acoustic signal source comprises a piezoelectric transducer.

37. The device according to claim 29, wherein the non-contact wave source comprises a speaker.

* * * * *